(12) United States Patent
Haviv et al.

(10) Patent No.: US 8,889,661 B2
(45) Date of Patent: Nov. 18, 2014

(54) TREATMENT OF LUPUS NEPHRITIS USING LAQUINIMOD

(75) Inventors: Asi Haviv, Kvutsat Shiller (IL); Nora Tarcic, Modiin (IL)

(73) Assignee: Teva Pharmaceutical Industries, Ltd., Petach-Tikva (IL)

( * ) Notice: Subject to any disclaimer, the term of this patent is extended or adjusted under 35 U.S.C. 154(b) by 430 days.

(21) Appl. No.: 13/039,178

(22) Filed: Mar. 2, 2011

(65) Prior Publication Data
US 2011/0218179 A1    Sep. 8, 2011

Related U.S. Application Data

(60) Provisional application No. 61/339,363, filed on Mar. 3, 2010.

(51) Int. Cl.
| A61K 31/56 | (2006.01) |
| A61K 31/47 | (2006.01) |
| A61K 31/5355 | (2006.01) |
| A61K 31/573 | (2006.01) |
| A61K 36/47 | (2006.01) |

(52) U.S. Cl.
CPC ............. *A61K 31/47* (2013.01); *A61K 31/5355* (2013.01); *A61K 31/573* (2013.01); *A61K 36/47* (2013.01)
USPC .......................... 514/171; 514/233.5; 514/312

(58) Field of Classification Search
USPC ...................................... 514/171, 233.5, 312
See application file for complete search history.

(56) References Cited

U.S. PATENT DOCUMENTS

| | | | |
|---|---|---|---|
| 4,107,310 | A | 8/1978 | Allais et al. |
| 4,547,511 | A | 10/1985 | Eriksoo et al. |
| 4,738,971 | A | 4/1988 | Eriksoo et al. |
| 4,782,155 | A | 11/1988 | Nakagawa et al. |
| 5,139,878 | A | 8/1992 | Kim et al. |
| 5,716,638 | A | 2/1998 | Touitou et al. |
| 5,912,349 | A | 6/1999 | Sih |
| 6,077,851 | A | 6/2000 | Bjork et al. |
| 6,121,287 | A | 9/2000 | Bjork et al. |
| 6,133,285 | A | 10/2000 | Bjork et al. |
| 6,307,050 | B1 | 10/2001 | Kwiatkowski et al. |
| 6,395,750 | B1 | 5/2002 | Hedlund et al. |
| 6,593,343 | B2 | 7/2003 | Bjork et al. |
| 6,605,616 | B1 | 8/2003 | Bjork et al. |
| 6,696,407 | B1 | 2/2004 | Longo et al. |
| 6,875,869 | B2 | 4/2005 | Jansson |
| 7,485,311 | B2 | 2/2009 | Lue et al. |
| 7,560,100 | B2 | 7/2009 | Pinchasi et al. |
| 7,560,557 | B2 | 7/2009 | Jansson |
| 7,589,208 | B2 | 9/2009 | Jansson et al. |
| 7,884,208 | B2 | 2/2011 | Frenkel et al. |
| 2002/0173520 | A1 | 11/2002 | Bjork et al. |
| 2005/0074451 | A1 | 4/2005 | Yednock et al. |
| 2005/0234238 | A1 | 10/2005 | Dube et al. |
| 2006/0004019 | A1 | 1/2006 | Lieberburg |
| 2007/0086979 | A1 | 4/2007 | Chevrier et al. |
| 2007/0207141 | A1 | 9/2007 | Lieberburg |
| 2007/0218062 | A1 | 9/2007 | Irving |
| 2007/0231319 | A1 | 10/2007 | Yednock |
| 2007/0293537 | A1 | 12/2007 | Patashnik et al. |
| 2008/0044382 | A1 | 2/2008 | Lieberburg |
| 2008/0063607 | A1 | 3/2008 | Tamarkin et al. |
| 2008/0090897 | A1 | 4/2008 | Steiner et al. |
| 2008/0108641 | A1 | 5/2008 | Ajami |
| 2008/0118553 | A1 | 5/2008 | Frenkel et al. |
| 2008/0166348 | A1 | 7/2008 | Kupper et al. |
| 2008/0206159 | A1 | 8/2008 | Tamarkin et al. |
| 2009/0048181 | A1 | 2/2009 | Schipper et al. |
| 2009/0062330 | A1 | 3/2009 | Kalafer et al. |
| 2009/0081259 | A1 | 3/2009 | Jonas et al. |
| 2009/0148462 | A1 | 6/2009 | Chevrier et al. |
| 2009/0156542 | A1 | 6/2009 | Purschke et al. |
| 2009/0162432 | A1 | 6/2009 | Safadi et al. |
| 2009/0221575 | A1 | 9/2009 | Gerber et al. |
| 2009/0232889 | A1 | 9/2009 | Jansson et al. |
| 2010/0055072 | A1 | 3/2010 | Gant et al. |
| 2010/0158903 | A1 | 6/2010 | Smith et al. |
| 2010/0209506 | A1 | 8/2010 | Eisenreich |
| 2010/0260716 | A1 | 10/2010 | Stohr et al. |
| 2010/0310547 | A1 | 12/2010 | Soliven |

(Continued)

FOREIGN PATENT DOCUMENTS

| EP | 1073639 | 11/2002 |
| EP | 1097139 | 11/2002 |

(Continued)

OTHER PUBLICATIONS

Ponticelli (Clin J Am Soc Nephrol, vol. 1, pp. 863-868; 2006).*
Morris et al. (Archives of Disease in Childhood, vol. 56, pp. 779-783; 1981).*
Galinsky et al. ["Basic Pharmacokinetics and Pharmacodynamics." in: Remington: The Science and Practice of Pharmacy (Baltimore, Lippincott Williams & Wilkins, 2006), p. 1171].*
Sabry et al, Int. Urol. Nephrol., 2009, 41, 153-161.*
Written Opinion of the International Searching Authority issued Aug. 19, 2010 in connection with PCT International Application No. PCT/US2010/01759, filed Jun. 18, 2010.

(Continued)

*Primary Examiner* — Jason Sims
*Assistant Examiner* — Ibrahim D Bori
(74) *Attorney, Agent, or Firm* — John P. White; Gary J. Gershik; Cooper & Dunham LLP

(57) ABSTRACT

This invention provides a method of treating a subject afflicted with active lupus nephritis comprising periodically administering to the subject an amount of laquinimod or pharmaceutically acceptable salt thereof effective to treat the subject. This invention also provides laquinimod or pharmaceutically acceptable salt thereof for use in treating a subject afflicted with active lupus nephritis. This invention further provides a pharmaceutical composition comprising an amount of laquinimod or pharmaceutically acceptable salt thereof for use in treating a subject afflicted with active lupus nephritis.

15 Claims, No Drawings

(56) References Cited

U.S. PATENT DOCUMENTS

| | | |
|---|---|---|
| 2010/0322900 A1 | 12/2010 | Tarcic et al. |
| 2011/0027219 A1 | 2/2011 | Tarcic et al. |
| 2011/0034508 A1 | 2/2011 | Hayardeny |
| 2011/0112141 A1 | 5/2011 | Frenkel et al. |
| 2011/0118308 A1 | 5/2011 | Frenkel et al. |
| 2011/0217295 A1 | 9/2011 | Haviv et al. |
| 2011/0218203 A1 | 9/2011 | Kaye et al. |
| 2011/0251235 A1 | 10/2011 | Patashnik et al. |
| 2012/0010238 A1 | 1/2012 | Piryatinsky et al. |
| 2012/0010239 A1 | 1/2012 | Fristedt |
| 2012/0142730 A1 | 6/2012 | Tarcic et al. |
| 2012/0225124 A1 | 9/2012 | Safadi et al. |
| 2012/0302600 A1 | 11/2012 | Patashnik et al. |
| 2013/0028866 A1 | 1/2013 | Gilgun et al. |
| 2013/0029916 A1 | 1/2013 | Gilgun et al. |

FOREIGN PATENT DOCUMENTS

| | | |
|---|---|---|
| EP | 1095021 | 9/2003 |
| EP | 1720531 | 11/2006 |
| EP | 1511732 | 12/2006 |
| WO | WO 99/55678 | 11/1999 |
| WO | WO 00/03991 | 1/2000 |
| WO | WO 00/03992 | 1/2000 |
| WO | WO 03/106424 | 12/2003 |
| WO | WO 2005/074899 | 8/2005 |
| WO | WO 2006/079653 | 8/2006 |
| WO | WO 2007/100770 | 9/2007 |
| WO | WO 2007/139887 | 12/2007 |
| WO | WO 2007/142667 | 12/2007 |
| WO | WO 2008/079270 | 7/2008 |
| WO | WO 2008/085484 | 7/2008 |
| WO | WO 2009/133468 | 11/2009 |
| WO | WO 2010/001257 | 1/2010 |
| WO | WO 2010/057006 | 5/2010 |

OTHER PUBLICATIONS

PCT International Search Report issued Aug. 19, 2010 in connection with PCT International Application No. PCT/US2010/01759, filed Jun. 18, 2010.
Written Opinion of the International Searching Authority issued Oct. 5, 2010 in connection with PCT International Application No. PCT/US2010/02194, filed Aug. 9, 2010.
PCT International Search Report issued Oct. 5, 2010 in connection with PCT International Application No. PCT/US2010/02194, filed Aug. 9, 2010.
Written Opinion of the International Searching Authority issued Sep. 7, 2010 in connection with PCT International Application No. PCT/US2010/02129 filed Jul. 29, 2010.
PCT International Search Report issued Sep. 7, 2010 in connection with PCT International Application No. PCT/US2010/02129 filed Jul. 29, 2010.
Written Opinion of the International Searching Authority issued Apr. 12, 2011 in connection with PCT International Application No. PCT/US2011/26879, filed Mar. 2, 2011.
PCT International Search Report issued Apr. 12, 2011 in connection with PCT International Application No. PCT/US2011/26879, filed Mar. 2, 2011.
Written Opinion of the International Searching Authority issued Apr. 29, 2011 in connection with PCT International Application No. PCT/US11/26885, filed Mar. 2, 2011.
PCT International Search Report issued Apr. 29, 2011 in connection with PCT International Application No. PCT/US11/26885, filed Mar. 2, 2011.
Written Opinion of the International Searching Authority issued May 19, 2011 in connection with PCT International Application No. PCT/US11/26891, filed Mar. 2, 2011.
PCT International Search Report issued May 19, 2011 in connection with PCT International Application No. PCT/US11/26891, filed Mar. 2, 2011.
Acheson, et al. (1995) "A BDNF autocrine loop in adult sensory neurons prevents cell death", Nature, 374(6521):450-3.
Alonso, et al. (2005) "Endogenous BDNF is required for long-term memory formation in the rat parietal cortex", Learning & Memory, 12:504-510.
Amaral, et al. (2007) "TRPC channels as novel effectors of BDNF signaling: Potential implications for Rett syndrome", Pharmacal Ther, 113(2007):394-409.
Barkhof, F. (1999) "MRI in Multiple Sclerosis: Correlation with Expanded Disability Status Scale (EDSS)", Multiple Sclerosis, 5(4):283-286.
Boneschi, et al. (2003) "Effects of glatiramer acetate on relapse rate and accumulated disbility in multiple sclerosis . . . ", Multiple Sclerosis, 9(4):349-355.
Caffe, et al. (2001) "A combination of CNTF and BDNF rescues rd photoreceptors . . . ", Investigative Ophthalmology & Visual Science, 42:275-82.
Chesselet, MF. (2003) "Dopamine and Parkinson's disease: is the killer in the house?" Molecular Psychiatry, 8:369-370.
Ciammola, et al. (2007) "Low brain-derived neurotrophic factor (BDNF) levels in serum of Huntington's disease patients", Am J Med Gent Part B, 144b:574-577.
ClinicalTrials.gov. Bethesda (MD): Natl Lib Med. Aug. 18, 2008 ID NCT00737932, Laquinimod Ph IIa Study . . . http://clinicaltrials.gov/ct2/show/NCT00737932?term=Crohns&recr=Open&rank=2.
Comi, et al. (2007) LAQ/5062 Study Group. "The Effect of Two Doses of Laguinimod . . . " Presented at 59th Ann. Mtg of the American Acad. of Neurology; Apr. 28-May 5, 2007 Boston, MA.
De Stefano, et al. (1999) "Evidence of early axonal damage in patients with multiple sclerosis", Arch Neural, 2001;58:65-70.
EMEA Guideline on Clinical Investigation of Medicinal Products for the Treatment of Multiple Sclerosis (CPMP/EWP/561/98 Rev. 1, Nov. 2006).
Hohlfeld, et al. (2000) "The neuroprotective effect of inflammation: implications for the therapy of multiple sclerosis", J Neuroimmunol, 107(2000):161-166.
Howells, et al. (2000) "Reduced BDNF mRNA expression in the Parkinson's disease substantia nigra", Experimental Neurology, 166(1):127-135.
Huang, EJ and Reichardt, LF (2001) "Neurotrophins: roles in neuronal development and function", Annu. Rev. Neurosci, 24:677-736.
Hyman, et al., (1991) "BDNF is a neurotrophic factor for dopaminergic neurons of the substantia nigra", Nature, 350(6315):230-2.
Katoh-Semba, et al. (2002) "Riluzole enhances expression of brain-derived neurotrophic factor with consequent proliferation . . . ", FASEB J, 16:1328-30.
Makar, et al. (2008) "Brain derived neurotrophic factor treatment reduces inflammation and apoptosis in . . . ", Journal of the Neurological Sciences, 270(1-2):70-76.
Miki, et al. (1999) "Relapsing-Remitting Multiple Sclerosis: Longitudinal Analysis of MR Images . . . ", Radiology, 213:395-399.
Mix, et al. (2008) "Animal models of multiple sclerosis for the development and validation of novel therapies—potential and limitations", Journal of Neurology, 255(6):7-14.
Molteni, et al. (2006) "Abstract: Chronic treatment with fluoxetine [Prozac®] up-regulates cellular BDNF mRNA expression in rat . . . ", Int J Neuropsychopharmacol, 9(3):307-17.
Monteggia, L. (2007) "Elucidating the role of brain-derived neurotrophic factor in the brain", Am J Psychiatry, 164:1790.
Neuhaus, et al. (2003) "Immunomodulation in multiple sclerosis: from immunosuppression to neuroprotection", Trends Pharmacol Sci, 24:131-138.
Noseworthy, et al. (2000) "Multiple sclerosis", N Engl J Med, 343:938-952.
Polman, et al. (2005) "Diagnostic criteria for multiple sclerosis: 2005 revisions to the McDonald Criteria", Annals of Neurology, 58(6):840-846.
Polman, et al. (2005) "Treatment with laquinimod reduces development of active MRI lesions in relapsing MS", Neurology, 64:987-991.
Preiningerova, J. (2009) "Oral laquinimod therapy in relapsing multiple sclerosis", Expert Opinion on Investigational Drugs, 18(7):985-989.

(56) References Cited

OTHER PUBLICATIONS

Riviere, M. (1998) "An analysis of extended survival in patients with amyotrophic lateral sclerosis treated with riluzole", Arch Neurol, 55:526-8.
Rudick, R. (1999) "Disease-Modifying Drugs for Relapsing-Remitting Multiple Sclerosis and Future Directions for . . . Therapeutics", Neurotherapeutics, 56:1079-1084.
Sandberg-Wollheim, et al. (2005) "48-Week Open Safety Study with a High-Dose Oral . . . " Therapy-Immunomodulation—Part II, Sep. 30, 2005, 15:30-17:00 (abstract only).
Sen, et al. (2008) "Serum brain-derived neurotrophic factor, depression, and antidepressant medications: mete-analyses and implications", Biol Psychiatry, 64:527-532.
Snider, et al. (1989) "Neurotrophic molecules", Ann Neural, 26(4):489-506.
Teva Press Release, "Laquinimod Demonstrated Significant and sustained Impact on Multiple Sclerosis Disease Activity", Sep. 18, 2008.
Tramontina, et al. (2009) "Brain-derived neurotrophic factor serum levels before and after treatment for acute mania", Neuroscience Letters, 452:111-3.
Tuvesson et al. (2005) "Cytochrome P450 3A4 is the major enzyme responsible for the metabolism of laquinimod, a novel immu . . . ", Drug Metabolism and Disposition. 33(6):866-872.
U.S. Appl. No. 13/800,047, filed Mar. 13, 2013, Kaye.
U.S. Appl. No. 13/874,537, filed May 1, 2013, Bar-Zohar.
U.S. Appl. No. 13/888,709, filed May 7, 2013, Laxer and Ulanenko.
U.S. Appl. No. 13/938,733, filed Jul. 10, 2013, Sarfati et al.
U.S. Appl. No. 13/939,306, filed Jul. 11, 2013, Kaye and Tarcic.
Apr. 5, 2013 Office Action issued in connection with Eurasian Patent Application No. 201290859.
May 6, 2013 Examination Report issued in connection with New Zealand Patent Application No. 602512.
Jun. 7, 2013 Supplementary European Search Report issued in connection with European Patent Application No. EP 11 75 1305.
Jun. 11, 2011 European Search Report issued in connection with Europe Patent Application No. 11751295.4.
Jun. 24, 2013 Communication Pursuant to Article 94(3) EPC issued in connection with European Patent Application No. 11751295.4.
Comi et al., "Effect of Laquinimod on MRI-monitored Disease Activity in Patients with Relapsing-remitting Multiple Sclerosis: . . . " Lancet, 371(9630): 2085-92 (2008).
Fauci et al., "Diagnostic Criteria for Systemic Lupus Erythematosus," Harrison's Principles of Internal Medicine (Eds.), McGraw Hill (New York), p. 2077 (2008).
Gordon et al., "Definition and treatment of lupus flares measured by the BILAG index," Rheumatol. 42, pp. 1372-1379 (2003).
Grossman et al., "Lupus Arthritis" Bailliere's Best Practice and Research. Clinical Reumatology, Bailliere Tindall, London, GB, vol. 23, No. 4, pp. 495-506(2009).
Sztejnbok et al., "Azathioprine in the Treatment of Systemic Lupus Erythematosus," Arthr. Rheum. 14, pp. 639-645 (1971).

Yee C-S et al., "BILAG-2004 Index Captures Systematic Lupus Erythematosus Diseases Activity Better than SLEDAI-2000," Ann. Rheum. Dis. 67, pp. 873-876 (2008).
Anonymous, "Laquinimod Study in Systematic Lupus Erythematosus (SLE) Patients with Active Lupus Nephritis," Mar. 4, 2010, Retrieved from the Internet.
Jul. 26, 2013 Office Action issued by the Chinese Patent Office in connection with Chinese Patent Application No. 201180012157.0, filed Sep. 3, 2012.
U.S. Appl. No. 13/650,060, filed Oct. 11, 2012, Hallak et al.
U.S. Appl. No. 13/712,398, filed Dec. 12, 2012, Tarcic et al.
U.S. Appl. No. 13/757,004, filed Feb. 1, 2013, Tarcic et al.
U.S. Appl. No. 13/768,919, filed Feb. 15, 2013, Ioffe et al.
PCT International Preliminary Report on Patentability issued Apr. 23, 2008 in connection with PCT International Application No. PCT/US2006/040925.
PCT International Preliminary Report on Patentability issued Sep. 4, 2012 in connection with PCT International Application No. PCT/US2011/026879.
PCT International Preliminary Report on Patentability issued Sep. 4, 2012 in connection with PCT International Application No. PCT/US2011/026885.
PCT International Preliminary Report on Patentability issued Sep. 4, 2012 in connection with PCT International Application No. PCT/US2011/026891.
Office Action issued by the U.S. Patent and Trademark Office on Nov. 5, 2012 in connection with U.S. Appl. No. 13/039,194.
Notice of Allowability issued by the U.S. Patent and Trademark Office on Feb. 15, 2013 in connection with U.S. Appl. No. 13/039,188.
Examination Report issued by the New Zealand Patent Office on Dec. 10, 2012 in connection with New Zealand Patent Application No. 602510.
Fauci et al. (2008) "Diagnostic Criteria for Systemic Lupus Erythematosus" in Harrison's Principles of Internal Medicine, (Eds.), McGraw Hill (New York), p. 2077.
Sztejnbok et al. (1971) "Azathioprine in the Treatment of Systemic Lupus Erythematosus" Arthr. Rheum. 14, 639-45.
Gordon et al. (2003) "Definition and treatment of lupus flares measured by the BILAG index" Rheumatol. 42, 1372-79.
Reagan-Shaw et al. (2007) "Dose translation from animal to human sturdies revisited" FASEB J 22:659-661.
"Guidance for Industry—Estimating the Maximum Safe Starting Dose in Initial Clinical Trials . . . " U.S. Department of Health and Health and Human Services . . . , Jul. 2005.
Mar. 13, 2014 Exam. Rpt. issued by the NZ Pat. Off. in connec. with NZ Pat. Appl. No. 602510, filed 9-19-2, nat'l stage of PCT Int'l Appl. No. PCT/US2011/026879, filed Mar. 2, 2011.
Apr. 8, 2014 Sec. O.A. issued by the CN Pat. Off. in connec. w/ CN Pat. Appl. No. 201180012157.0, filed Sep. 3, 2012. nat'l stage of PCT Int'l Appl. PCT/US2011/026879, filed Mar. 2, 2011.
Aug. 8, 2014 Official Action issued by the Eurasian Patent Office in connection with Eurasian Patent Application No. 201290837 (w/ English language translation).

\* cited by examiner

TREATMENT OF LUPUS NEPHRITIS USING LAQUINIMOD

This application claims the benefit of U.S. Provisional Application No. 61/339,363, filed Mar. 3, 2010, the entire content of which is hereby incorporated by reference herein.

Throughout this application, various publications are referred to by first author and year of publication. Full citations for these publications are presented in a References section immediately before the claims. Disclosures of the publications cited in the References section in their entireties are hereby incorporated by reference into this application in order to more fully describe the state of the art as of the date of the invention described herein.

BACKGROUND

Lupus Nephritis (LN)

Lupus nephritis (LN), characterized by inflammation of the kidney, is a complication which occurs in a subpopulation of patients with Systemic Lupus Erythematosus (SLE) and is one of the most serious complications caused by SLE. (MedlinePlus)

SLE is a debilitating autoimmune disease of great clinical diversity and can manifest itself in different ways and lead to a number of complications, e.g., arthritis, arthralgia, and myalgia, depending on the patient and the parts of the body affected. The precise etiology of SLE has not yet been determined, but hormonal, genetic, viral and environmental factors may precipitate the disease. SLE prevalence varies across ethnicities and geographic regions with an occurrence rate of 15 to 50 cases per 100,000 persons. SLE is most common in women of childbearing age (15-44) with a female-to-male ratio varying from 4.3 to 13.6 (Petri, 2002). Virtually all body systems may be involved, including the musculoskeletal, mucocutaneous, cardiovascular, neurological, respiratory, renal, ophthalmic hematological and gastrointestinal systems.

Due to the great clinical diversity and idiopathic nature of SLE, management of idiopathic SLE depends on its specific manifestations and severity. (The Merck Manual, 1999) Therefore, medications suggested to treat SLE generally are not necessarily effective for the treatment of all manifestations of and complications resulting from SLE, e.g., LN.

LN usually arises early in the disease course, within 5 years of diagnosis. The pathogenesis of LN is believed to derive from deposition of immune complexes in the kidney glomeruli that initiates an inflammatory response (Brent, 2008).

An estimated 30-50% of patients with SLE develop nephritis that requires medical evaluation and treatment. LN is a progressive disease, running a course of clinical exacerbations and remissions. Early detection and treatment can significantly improve renal outcome and prognosis. Although over the last decades, treatment of LN has been greatly improved, 5 and 10-year survival rates are documented as 85% and 73%, respectively (Brent, 2008). LN morbidity is related to the renal disease itself, as well as to treatment-related complications.

Renal biopsy is considered for any patient with SLE who has clinical or laboratory evidence of active nephritis, in order to determine the histological type as well as the appropriate treatment management and prognosis. (Bevra, 2001; Brent, 2008)

The histological classification of LN was revised by the International Society of Pathology/Renal Pathology Society (ISN/RPS) in 2003 and is based on light microscopy, immunofluorescence, and electron microscopy findings from renal biopsy specimens (Foster, 2004). These classifications describes 6 major classes of LN: Class I and II—mesangial LN, Class III and IV—proliferative LN, class V—membranous LN and class VI—advanced sclerosis LN. The ISN/RPS classifications were based on earlier classifications by the World Health Organization (WHO) published in 1974 and 1982.

There is no definitive treatment or cure for LN. The principal goals of therapy is to normalize renal function, urine sediment and proteinuria, reduce the frequency of relapses or prevent the progressive loss of renal function through mild, moderate and severe renal impairment to end stage renal disease (ESRD) requiring dialysis or kidney transplantation. Therapy varies pending on the histopathological findings as well as the clinical manifestations.

Corticosteroids and cytotoxic or immunosuppressive agents, particularly cyclophosphamide, azathioprine, or mycophenolate mofetil (MMF) are the standard of care for patients with aggressive proliferative LN, while less aggressive treatment options may be considered for purely membranous LN or mesangial LN. Angiotensin Converting Enzyme (ACE) inhibitors or Angiotensin II Receptor Blockers (ARBs) may control blood pressure and reduce proteinuria.

Most of the above mentioned treatments are not specifically indicated for the treatment of SLE/LN and treatment protocols vary.

Treatment of accompanying SLE signs, symptoms, and complications may additionally include a combination of NSAIDs, antimalarial agents, antihypertensives, calcium supplements or bisphosphonate, anti-coagulants and others.

While many patients fail to respond or respond only partially to the standard of care medications listed above, the long-term use of high doses of corticosteroids and cytotoxic therapies may have profound side effects such as bone marrow depression, increased infections with opportunistic organisms, irreversible ovarian failure, alopecia and increased risk of malignancy. Infectious complications coincident with active SLE and its treatment with immunosuppressive medications are the most common cause of death in patients with SLE.

There is, therefore, a need for alternative therapies with better risk-benefit profiles for the treatment of lupus nephritis.

Laquinimod is a novel synthetic compound with high oral bioavailability which has been suggested as an oral formulation for the treatment of Multiple Sclerosis (MS) (Polman, 2005; Sandberg-Wollheim, 2005). Laquinimod and its sodium salt form are described, for example, in U.S. Pat. No. 6,077,851. The effects of laquinimod on lupus nephritis have not been reported.

Mycophenolate Mofetil (MMF)

Mycophenolate mofetil (MMF), sold under the brand name CellCept®, is the 2-morpholinoethyl ester of mycophenolic acid (MPA), an immunosuppressive agent, and inosine monophosphate dehydrogenases (IMPDH) inhibitor. The chemical name for mycophenolate mofetil (MMF) is 2-morpholinoethyl (E)-6-(1,3-dihydro-4-hydroxy-6-methoxy-7-methyl-3-oxo-5-isogenzofuranyl)-4-methyl-4-hexenoate. It has an empirical formula of $C_{23}H_{31}NO_7$ and a molecular weight of 433.50. CellCept® is indicated for prophylaxis of organ rejection in patients receiving allogeneic renal, cardiac or hepatic transplants (Physician's Desk Reference, 2009).

CellCept® is available for oral administration as capsules containing 250 mg of mycophenolate mofetil, tablets containing 500 mg of mycophenolate mofetil, and as a powder for oral suspension, which when constituted contains 200 mg/mL mycophenolate mofetil. CellCept® is also available for Intravenous administration as a sterile white to off-white lyophilized powders in vials containing mycophenolate mofetil hydrochloride. Each vial of IV contains the equivalent of 500 gm MMF as the hydrochloride salt. The recommended dose for CellCept® is 1 g administered orally or via IV (over no less than 2 hours) twice daily (daily dose of 2 g) for use in renal transplant patients. The recommended dose of CellCept® oral suspension is 600 mg/m2 administered twice daily up to a maximum daily dose of 2 g/1-mL oral suspension (Physician's Desk Reference, 2009).

Combination Therapy

The administration of two drugs to treat a given condition, such as a form of lupus, raises a number of potential problems. In vivo interactions between two drugs are complex. The effects of any single drug are related to its absorption, distribution, and elimination. When two drugs are introduced into the body, each drug can affect the absorption, distribution, and elimination of the other and hence, alter the effects of the other. For instance, one drug may inhibit, activate or induce the production of enzymes involved in a metabolic route of elimination of the other drug (Guidance for Industry, 1999). Thus, when two drugs are administered to treat the same condition, it is unpredictable whether each will complement, have no effect on, or interfere with, the therapeutic activity of the other in a human subject.

Not only may the interaction between two drugs affect the intended therapeutic activity of each drug, but the interaction may increase the levels of toxic metabolites (Guidance for Industry, 1999). The interaction may also heighten or lessen the side effects of each drug. Hence, upon administration of two drugs to treat a disease, it is unpredictable what change will occur in the negative side profile of each drug.

Additionally, it is difficult to accurately predict when the effects of the interaction between the two drugs will become manifest. For example, metabolic interactions between drugs may become apparent upon the initial administration of the second drug, after the two have reached a steady-state concentration or upon discontinuation of one of the drugs (Guidance for Industry, 1999).

SUMMARY OF THE INVENTION

This invention provides a method of treating with active lupus nephritis comprising periodically administering to the subject an amount of laquinimod or pharmaceutically acceptable salt thereof effective to treat the subject.

This invention also provides laquinimod or pharmaceutically acceptable salt thereof for use in treating a subject afflicted with active lupus nephritis.

This invention further provides a pharmaceutical composition comprising an amount of laquinimod or pharmaceutically acceptable salt thereof for use in treating a subject afflicted with active lupus nephritis.

DETAILED DESCRIPTION OF THE INVENTION

This invention provides a method of treating a subject afflicted with active lupus nephritis comprising periodically administering to the subject an amount of laquinimod or pharmaceutically acceptable salt thereof effective to treat the subject.

In one embodiment, the pharmaceutically acceptable salt of laquinimod is laquinimod sodium.

In one embodiment, the periodic administration of laquinimod or pharmaceutically acceptable salt thereof is effected orally. In another embodiment, the amount of laquinimod administered is 0.5-1.0 mg/day. In another embodiment, the amount of laquinimod administered is 0.5 mg/day. In yet another embodiment, the amount of laquinimod administered is 1.0 mg/day.

In one embodiment, the amount of laquinimod or pharmaceutically acceptable salt thereof is effective to reduce a clinical symptom of active lupus nephritis in the subject. In another embodiment, the periodic administration of laquinimod or pharmaceutically acceptable salt thereof is effective to elicit at least a partial response by the subject by week 24. In yet another embodiment, the periodic administration of laquinimod or pharmaceutically acceptable salt thereof is effective to elicit a complete response by the subject by week 24.

In one embodiment, the periodic administration of laquinimod or pharmaceutically acceptable salt thereof reduces proteinuria in the subject. In the other embodiment, the proteinuria reduction is measured by 24 hour urine protein, 24 hour protein to creatinine ratio, spot protein to creatinine ratio, 24 hour urine albumin, 24 hour albumin to creatinine ratio, spot albumin to creatinine ratio, or by a urinary dipstick.

In one embodiment, the periodic administration of laquinimod or pharmaceutically acceptable salt thereof reduces the subject's protein to creatinine ratio. In another embodiment, the subject's protein to creatinine ratio is reduced by at least 50% as compared to baseline. In another embodiment, the subject's protein to creatinine ratio is reduced to no more than 0.3. In another embodiment, the subject's protein to creatinine ratio is less than 3 and wherein the subject's serum creatinine level is either less than 1.3 mg/dL or did not increase by more than 10% relative to baseline. In yet another embodiment, the subject's protein to creatinine ratio is less than 0.5 and wherein the subject's serum creatinine level is either less than 1.3 mg/dL or decreased by at least 25% relative to baseline.

In one embodiment, the period administration of laquinimod or pharmaceutically acceptable salt thereof eliminates urinary sediments.

In one embodiment, the periodic administration of laquinimod or pharmaceutically acceptable salt thereof improves the subject's BILAG index In one embodiment, the method further comprises administration of mycophenolate mofetil. In another embodiment, the periodic administration of mycophenolate mofetil is effected orally. In another embodiment, the amount of mycophenolate mofetil administered is 1-3 g/day. In yet another embodiment, the amount of mycophenolate mofetil administered is 2 g/day.

In one embodiment, the method further comprises administering to the subject an amount of a steroid. In another embodiment, the administration of the steroid is periodic administration. In another embodiment, the administration of steroids is effected orally and/or intravenously. In another embodiment, the amount of steroid administered is 500 mg/day methylprednisolone. In yet another embodiment, the amount of steroid administered is 40 mg/day prednisolone and/or prednisone.

In one embodiment, the method further comprises administration of angiotensin converting enzyme (ACE) inhibitors, angiotensin receptor blockers (ARBs), antimalarials, statins, cyclophosphamide, azathioprine, 6-mercaptopurine, abatacept, rituximab, belimumab, cyclosporine or other calcineurin inhibitors.

In one embodiment, the periodic administration continues for at least 24 weeks.

In one embodiment, the amount of laquinimod or pharmaceutically acceptable salt thereof and the amount of mycophenolate mofetil together is effective to reduce a clinical symptom of active lupus nephritis in the subject. In another embodiment, the periodic administration of laquinimod or pharmaceutically acceptable salt thereof and mycophenolate mofetil is effective to elicit at least a partial response by the subject by week 24. In yet another embodiment, the periodic administration of laquinimod or pharmaceutically acceptable salt thereof and mycophenolate mofetil is effective to elicit a complete response by the subject by week 24.

In one embodiment, the periodic administration of laquinimod or pharmaceutically acceptable salt thereof and mycophenolate mofetil reduces proteinuria in the subject. In the other embodiment, the proteinuria reduction is measured by 24 hour urine protein, 24 hour protein to creatinine ratio, spot protein to creatinine ratio, 24 hour urine albumin, 24 hour albumin to creatinine ratio, spot albumin to creatinine ratio, or by a urinary dipstick.

In one embodiment, the periodic administration of laquinimod or pharmaceutically acceptable salt thereof and mycophenolate mofetil reduces the subject's protein to creatinine ratio. In another embodiment, the subject's protein to creatinine ratio is reduced by at least 50% as compared to baseline. In another embodiment, the subject's protein to creatinine ratio is reduced to no more than 0.3. In another embodiment, the subject's protein to creatinine ratio is less than 3 and wherein the subject's serum creatinine level is either less than 1.3 mg/dL or did not increase by more than 10% relative to baseline. In yet another embodiment, the subject's protein to creatinine ratio is less than 0.5 and wherein the subject's serum creatinine level is either less than 1.3 mg/dL or decreased by at least 25% relative to baseline.

In one embodiment, the period administration of laquinimod or pharmaceutically acceptable salt thereof and mycophenolate mofetil eliminates urinary sediments.

In one embodiment, the periodic administration of laquinimod or pharmaceutically acceptable salt thereof and mycophenolate mofetil improves the subject's BILAG index.

In one embodiment, each of the amount of laquinimod or pharmaceutically acceptable salt when taken alone, and the amount of mycophenolate mofetil when taken alone is effective to treat the subject. In another embodiment, either the amount of laquinimod or pharmaceutically acceptable salt when taken alone, the amount of mycophenolate mofetil when taken alone, or each such amount when taken alone is not effective to treat the subject.

In one embodiment, the subject is receiving mycophenolate mofetil therapy prior to initiating laquinimod therapy. In another embodiment, the subject initiates periodic mycophenolate mofetil administration prior to initiating periodic laquinimod administration.

In one embodiment, the administration of the laquinimod or pharmaceutically acceptable salt thereof substantially precedes the administration of mycophenolate mofetil. In another embodiment, the administration of mycophenolate mofetil substantially precedes the administration of laquinimod or pharmaceutically acceptable salt thereof.

In one embodiment, the subject is human.

This invention provides a method of treating active lupus nephritis in a subject afflicted therewith comprising periodically administering to the subject an amount of laquinimod or pharmaceutically acceptable salt thereof effective to treat the active lupus nephritis in the subject.

This invention also provides laquinimod or pharmaceutically acceptable salt thereof for use in treating a subject afflicted with active lupus nephritis. This invention also provides laquinimod or pharmaceutically acceptable salt thereof for use in combination with mycophenolate mofetil for treating a subject afflicted active lupus nephritis.

This invention also provides laquinimod or pharmaceutically acceptable salt thereof for use in treating active lupus nephritis. This invention also provides laquinimod or pharmaceutically acceptable salt thereof for use in combination with mycophenolate mofetil for treating active lupus nephritis.

This invention also provides a pharmaceutical composition comprising an amount of laquinimod or pharmaceutically acceptable salt thereof for use in treating a subject afflicted with active lupus nephritis. This invention further provides a pharmaceutical composition comprising an amount of laquinimod or pharmaceutically acceptable salt thereof and an amount of mycophenolate mofetil for use in treating a subject afflicted with active lupus nephritis.

For the foregoing embodiments, each embodiment disclosed herein is contemplated as being applicable to each of the other disclosed embodiment.

It is understood that where a parameter range is provided, all integers within that range, and tenths thereof, are also provided by the invention. For example, "1-3 g/day" includes 1.0 g/day, 1.1 g/day, 1.2 g/day, 1.3 g/day, 1.4 g/day etc. up to 3.0 g/day.

Disclosed is a method of treating a subject afflicted with lupus, specifically, lupus nephritis, using laquinimod with standard of care, i.e., Mycophenolate Mofetil and Steroids, which provides a more efficacious treatment of the subject afflicted with lupus nephritis. As described herein, administration of laquinimod with standard of care, i.e., Mycophenolate Mofetil and Steroids, is particularly effective in combination to treat the subject afflicted with lupus nephritis.

Terms

As used herein, and unless stated otherwise, each of the following terms shall have the definition set forth below.

As used herein, an "amount" or "dose" of laquinimod as measured in milligrams refers to the milligrams of laquinimod acid present in a preparation, regardless of the form of the preparation. Therefore, a "dose of 0.5 mg laquinimod" means the amount of laquinimod acid in a preparation is 0.5 mg, regardless of the form of the preparation. Similarly, a "dose of 1 mg laquinimod" means the amount of laquinimod acid in a preparation is 1 mg, regardless of the form of the preparation. Thus, when in the form of a salt, e.g. a laquinimod sodium salt, the weight of the salt form necessary to provide a dose of 0.5 mg laquinimod would be greater than 0.5 mg due to the presence of the additional salt ion.

As used herein, "laquinimod" means laquinimod acid or a pharmaceutically acceptable salt thereof.

As used herein, "a subject afflicted with active lupus nephritis" means a subject who was been affirmatively diagnosed to have active lupus nephritis.

As used herein, "effective" when referring to an amount of laquinimod, MMF or steroids refers to the quantity of laquinimod, MMF or steroids that is sufficient to yield a desired therapeutic response without undue adverse side effects (such as toxicity, irritation, or allergic response) commensurate with a reasonable benefit/risk ratio when used in the manner of this invention.

As used herein, "treating" encompasses, e.g., inducing inhibition, regression, or stasis of a disorder, or lessening, suppressing, inhibiting, reducing the severity of, eliminating, or ameliorating a symptom of the disorder.

As used herein, "inhibition" of disease progression or disease complication in a subject means preventing or reducing the disease progression and/or disease complication in the subject.

As used herein, a "loading dose" refers to an initial higher dose of a drug that may be given at the beginning of a course of treatment before dropping down to a lower "intended dose" or "maintenance dose".

As used herein, a "symptom" associated with lupus nephritis includes any clinical or laboratory manifestation associated with lupus nephritis and is not limited to what the subject can feel or observe. Proteinuria is a symptom of lupus nephritis.

As used herein, "complete response (CR)" means protein to creatinine ratio <0.5 and [decreased serum creatinine by at least 25% compared to baseline or serum creatinine <1.3 mg/dL].

As used herein, "partial response (PR)" means criteria for complete response are not met and at least 50% decrease in protein to creatinine ratio and protein to creatinine ratio <3 with stable serum creatinine (serum creatinine <1.3 mg/dL or did not increase by more than 10% from baseline).

As used herein, "glomerular filtration rate" or "GFR" is a measure of renal function. GFR is the volume of fluid filtered from the renal (kidney) glomerular capillaries into the Bowman's capsule per unit time. GFR can be calculated by measuring any chemical that has a steady level in the blood, and is freely filtered but neither reabsorbed nor secreted by the kidneys. The rate therefore measured is the quantity of the substance in the urine that originated from a calculable volume of blood. The GFR is typically recorded in units of volume per time, e.g. milliliters per minute ml/min.

As used herein, "The British Isles Lupus Assessment Group Index" or "BILAG" index is a validated comprehensive computerized index for measuring clinical disease activity in systemic lupus erythematosus (SLE), which was developed according to the principle of the physician's 'intention to treat'.

A BILAG assessment consists of 97 variables, some based on the patient's history, some on examination findings and others on laboratory/imaging results. The questions are grouped under nine systems: Constitutional, Mucocutaneous, Neuropsychiatric, Musculoskeletal, Cardiorespiratory, Gastrointestinal, Ophthalmic, Renal and Hematological.

The index attempts to capture only SLE related disease activity in the previous 4 weeks prior to each assessment. Each of the clinical variables may be recorded as:
0. Absent.
1. Improved. Sufficient for considering reduction in therapy and [improvement present on assessment and for at least 2 weeks or completely resolved within the entire last week].
2. Same. No improvement and no deterioration within the last 4 weeks compared to the previous 4 weeks or improvement does not meet improvement criteria.
3. Worse. Deteriorated during the last 4 weeks compared to the previous 4 weeks.
4. New. New or recurrent episode during the last 4 weeks (compared to the previous 4 weeks), which is not improving.

Based upon the scoring to each of these variables, a predefined algorithm, specific for each system, provides a disease activity score ranging from A to E for each system:
Grade 'A'=severe disease activity requiring treatment with high dose steroids (>20 mg/day oral prednisolone or equivalent or IV pulse >500 mg MP), systemic immunomodulators or high dose anticoagulation
Grade 'B'=moderate disease activity requiring treatment with low dose oral steroids (<20 mg/day prednisolone or equivalent), IM or IA steroids (equivalent to MP<500 mg), topical steroids or immunomodulators, antimalarials or symptomatic therapy (e.g. NSAIDS).
Grade 'C'=mild disease.
Grade 'D'=indicates previously affected but currently inactive.
Grade 'E'=this system has never been involved.

As used herein, "Evaluator/physician Global Assessment (EGA)" is a Visual Analogue Scale. It measures the disease activity based on the physician subjective assessment from none active to worse disease activity. EGA is performed at every visit (except for screening).

As used herein, "Patient Global Assessment (PGA)" is a Visual Analogue Scale. It measures the subject perception of his/hers overall health condition, from very well to very poor.

As used herein, an "adverse event" or "AE" means any untoward medical occurrence in a clinical trial subject administered a medicinal product and which does not have a causal relationship with the treatment. An adverse event can therefore be any unfavorable and unintended sign including an abnormal laboratory finding, symptom, or diseases temporally associated with the use of an investigational medicinal product, whether or not considered related to the investigational medicinal product.

As used herein, "pharmaceutically acceptable carrier" refers to a carrier or excipient that is suitable for use with humans and/or animals without undue adverse side effects (such as toxicity, irritation, and allergic response) commensurate with a reasonable benefit/risk ratio. It can be a pharmaceutically acceptable solvent, suspending agent or vehicle, for delivering the instant compounds to the subject.

When referring to dosing, the designation "BID" indicates that the dose is administered twice daily. The designation "QD" indicates that the dose is administered once daily.

A number of experiments were conducted testing for the effects of laquinimod on lupus manifestations using murine models. (see Examples 1.1-1.4) However, the effects of laquinimod on lupus nephritis in humans have not been reported. Therefore, based on the encouraging results of these experiments, a clinical trial is initiated (See Example 2).

The use of laquinimod for SLE had been previously suggested in, e.g., U.S. Pat. No. 6,077,851. However, without empirical evidence, one cannot affirmatively establish that laquinimod will be effective for treating all complications arising from SLE based on this disclosure alone. The '851 patent does not disclose the use of laquinimod for the particular sub-population of SLE relevant to the instant invention. That is, the '851 patent does not disclose the use of laquinimod for lupus nephritis. On the other hand, the inventors have surprisingly found that laquinimod is particularly effective for the treatment of lupus nephritis.

Further, the inventors have surprisingly found that the combination of laquinimod and MMF is particularly effective for the treatment of lupus nephritis as compared to each agent alone.

A pharmaceutically acceptable salt of laquinimod as used in this application includes lithium, sodium, potassium, magnesium, calcium, manganese, copper, zinc, aluminum and iron. Salt formulations of laquinimod and the process for preparing the same are described, e.g., in U.S. Patent Application Publication No. 2005/0192315 and PCT International Application Publication No. WO 2005/074899, which are hereby incorporated by reference into this application.

A dosage unit may comprise a single compound or mixtures of compounds thereof. A dosage unit can be prepared for oral dosage forms, such as tablets, capsules, pills, powders, and granules.

Laquinimod can be administered in admixture with suitable pharmaceutical diluents, extenders, excipients, or carriers (collectively referred to herein as a pharmaceutically acceptable carrier) suitably selected with respect to the intended form of administration and as consistent with conventional pharmaceutical practices. The unit is preferably in a form suitable for oral administration. Laquinimod can be administered alone but is generally mixed with a pharmaceutically acceptable carrier, and co-administered in the form of a tablet or capsule, liposome, or as an agglomerated powder. Examples of suitable solid carriers include lactose, sucrose, gelatin and agar. Capsule or tablets can be easily formulated and can be made easy to swallow or chew; other solid forms include granules, and bulk powders. Tablets may contain suitable binders, lubricants, disintegrating agents, coloring agents, flavoring agents, flow-inducing agents, and melting agents. For instance, for oral administration in the dosage unit form of a tablet or capsule, the active drug component can be combined with an oral, non-toxic, pharmaceutically acceptable, inert carrier such as lactose, gelatin, agar, starch, sucrose, glucose, methyl cellulose, dicalcium phosphate, calcium sulfate, mannitol, sorbitol, microcrystalline cellulose and the like. Suitable binders include starch, gelatin, natural sugars such as glucose or beta-lactose, corn starch, natural and synthetic gums such as acacia, tragacanth, or sodium alginate, povidone, carboxymethylcellulose, polyethylene glycol, waxes, and the like. Lubricants used in these dosage forms include sodium oleate, sodium stearate, sodium benzoate, sodium acetate, sodium chloride, stearic acid, sodium stearyl fumarate, talc and the like. Disintegrators include, without limitation, starch, methyl cellulose, agar, bentonite, xanthan gum, croscarmellose sodium, sodium starch glycolate and the like.

Specific examples of the techniques, pharmaceutically acceptable carriers and excipients that may be used to formulate oral dosage forms of the present invention are described, e.g., in U.S. Patent Application Publication No. 2005/0192315, PCT International Application Publication Nos. WO 2005/074899, WO 2007/047863, and WO 2007/146248.

General techniques and compositions for making dosage forms useful in the present invention are described in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modern Pharmaceutics Drugs and the Pharmaceutical Sciences, Vol. 40 (Gilbert S. Banker, Christopher T. Rhodes, Eds.). These references in their entireties are hereby incorporated by reference into this application.

This invention will be better understood by reference to the Experimental Details which follow, but those skilled in the art will readily appreciate that the specific experiments detailed are only illustrative of the invention as described more fully in the claims which follow thereafter.

EXPERIMENTAL DETAILS

Example 1

Assessment of the Effect of Laquinimod for SLE in Animal Models

Systemic Lupus Erythematosus (SLE) is a disorder of generalized autoimmunity characterized by defective T cell-mediated responses and the formation of a variety of antibodies reactive to self or altered self-antigens. SLE is mainly characterized by the presence of anti-DNA antibodies. Some of these auto-antibodies combine with the corresponding auto-antigens, forming immune complexes, either in the circulating blood or directly in tissues, resulting in severe damage. Glomerulonephritis induced by immune complexes is in fact the major cause of death in patients with SLE. (NZBxNZW) F1 are lupus-prone mice that develop an SLE-like disease spontaneously including anti-dsDNA antibodies (Abs), proteinuria and Immune Complex Deposits (ICD). The (NZBxNZW)F1 (NZB/W) murine model is the hallmark of spontaneous SLE.

In a number of studies, the effect of various doses of laquinimod in the (NZBxNZW)F1 model for SLE were assessed. The studies also included a negative control (water) and positive controls including cyclophosphamide (CTX) and methotrexate (MTX).

Example 1.1

Effect of Laquinimod, Cytoxan (CTX), and Methotrexate (MTX) on Lupus Manifestations Using the (NZBxNZW)F1 Mouse Model This study investigated the effect of laquinimod, an immunomodulator of SLE in a murine model of SLE and compared the treatment effect to reference substances CTX and MTX. CTX is an alkylating agent that has become the standard of care for the disease management of most severe forms of lupus. MTX is an antimetabolite drug used in treatment of cancer and autoimmune diseases. It acts by inhibiting the metabolism of folic acid via the inhibition of dihydrofolate reductase and blocks DNA synthesis in rapidly proliferate cells. These actions include immunosuppression. Both CTX and MTX have shown efficacy in prior studies.

Laquinimod and reference compounds CTX and MTX were applied in therapeutic mode, starting the treatment at the time when the characteristic change of murine SLE model, proteinuria (PU) was present in >80% of animals, and the observation and treatment period following this was 12 weeks. Laquinimod was applied p.o. daily, in a dose of 25 mg/kg. CTX was applied once weekly in a dose of 25 mg/ig i.p. MTX was applied 3 times a week p.o. at 35 µg/mouse.

Also, body weight changes were recorded weekly and at the end of experiment both kidneys were preserved, one for possible conventional histology and one for immune complex detection (ICD) in glomeruli. Evaluation of ICD was performed by scoring and by image analysis.

80 animals were involved in the study. During the treatment period 4 animals died, 2 from the vehicle treated group and 2 from the MTX treated group.

The severity of disease followed by PU measurement showed gradual increase in the control (water treated, vehicle) group, but substantial difference between the treated and vehicle groups developed around the 8-12$^{th}$ week of observation. At Week 12 observation, laquinimod and CTX treatment significantly diminished the proteinuria (p<0.01 and P<0.05 by MW U test, respectively).

At the end of experiment ICD was evaluated by two methods, and the results from the two methods showed good correlation (correlation coefficient: 0.993). The immune complex deposition was significantly inhibited by laquinimod and CTX (p<0.001 and p<0.05, respectively)—the results correlate well with the PU data on the last week (correlation coefficient of group averages of ICD and PU: 0.8199).

Therefore, laquinimod and the reference drug CTX significantly diminished the proteinuria and immune complex deposition in kidney of murine SLE model. MTX failed to inhibit the symptoms.

Example 1.2

Confirmation of Efficacy of Laquinimod in the (NZBxNZW)F1 Model for SLE—Dose Response Study This was a survival dose response study to determine whether laquinimod is effective in suppressing the symptoms in (NZBxNZW)F1 mice. The positive control used was Cytoxan.

Seventy-one mice having spontaneous disease developed by the age of 7 months (as measured by proteinuria) were divided into 6 experimental groups (Water, CTX, Laquinimod 0.2 mg/kg, Laquinimod 1.0 mg/kg, Laquinimod 5.0 mg/kg, Laquinimod 25.0 mg/kg) according to their PU scores.

Water and Laquinimod were administered orally (200 µl/mouse) 5 days a week. CTX was administered intraperitonealy once weekly, (200 µl/mouse). Blood samples were collected on Weeks 1, 5, 15 and 37. Serum samples were prepared for detection of anti-dsDNA antibodies. After 37 weeks (257 days) of treatment, mice were sacrificed.

The study revealed that laquinimod treatment inhibited the clinical symptoms of disease in NZB/W mice, specifically proteinuria and anti-dsDNA levels resulting in prolonged survival. Treatment with all doses of laquinimod abrogated the progression of proteinuria in comparison to vehicle treatment, while the specific doses of 1, 5, and 25 mg/kg were as effective as the positive control cyclophosphamide (CTX). The dose of 0.2 mg/ml abrogated proteinuria but not to the same extent as compared to the higher doses. In terms of anti-dsDNA levels, there was a dose dependent reduction in antibody levels over time. Finally, all doses resulted in significant prolongation of survival.

Example 1.3

Confirmation of Efficacy of Laquinimod in the (NZBxNZW)F1 Model for SLE

This study examined the effect of laquinimod (0.2 and 5 mg/kg) versus CTX and vehicle treated (NZBxNZZW)F1 mice.

Seventy mice having spontaneous disease developed by the age of 7 months (as measured by proteinuria) were divided into 4 experimental groups (Water, CTX, Laquinimod 0.2 mg/kg, Laquinimod 5.0 mg/kg,) according to their PU scores.

Water and Laquinimod were administered orally (200 µl/mouse) 5 days a week. CTX was administered intraperitonealy once weekly, (200 µl/mouse). Blood samples were collected on Weeks 1, 5, and 11. Serum samples were prepared for detection of anti-dsDNA antibodies. After 13 weeks of treatment, mice were sacrificed and immune complex deposits in their kidneys were evaluated.

This study confirms that laquinimod abrogated disease progression in NZB/W mice as measured by proteinuria. When looking at other endpoints, specifically anti-dsDNA levels and immune complex deposits, treatment with 5 mg/kg behaved similarly to the positive control CTX. Treatment at the low dose (0.2 mg/kg) prevented increased proteinuria but did not inhibit anti-dsDNA Ab titers and ICD.

Example 1.4

Non-GLP In Vivo Evaluation of Laquinimod in the MRL/lpr Lupus Mouse Model

This study evaluates the efficacy of laquinimod in the MRL/lpr lupus mouse model.

Animals were monitored until their urine proteinuria reached >200 mg/dL at which time they were enrolled in the study. Animals were dosed with either 1 or 5 mg/kg of laquinimod, p.o., 100 mg/kg mycophenolate mofetil (MMF, CellCept®) p.o., or vehicle (water DDW), p.o., daily except weekends.

Proteinuria, ankle and paw diameters, dsDNA autoantibody levels and survival were monitored during in life portion of the study. At termination, blood samples were harvested for determination of dsDNA autoantibody levels, spleens were harvested and weighed then processed to isolate splenocytes which were counted. Kidney, lung, skin, lymph node, salivary gland and joints were harvested, processed for histological examination and scored by a histopathologist blind to the treatments.

Overall there appeared to be a trend toward dose dependent efficacy in the animals treated with laquinimod in the measures during the in life phase of the experiment. The high variability in the data resulted in these trends not being significant except for some sporadic time points. Histopathological analysis of the kidney reveled significant reductions in kidney glomerulonephritis with MMF and laquinimod treatment at 5 mg/kg treatment compared to vehicle treatment. A significant difference was detected between MMF treatment and vehicle treatment group for the lung BALT hyperplasia. There were no effects of any of the test article treatments on the histopathology of the skin or lymph nodes. When the salivary gland inflammation was evaluated by histopathological scoring, a significant reduction was seen with both MMF and 5 mg/kg laquinimod treatments compared to vehicle treatment. Significant reductions in bone resorption were seen with both doses of laquinimod compared to vehicle control. A significant reduction in cartilage damage was detected with laquinimod treatment at 5 mg/kg compared to vehicle treatment. A significant reduction in inflammation of the joints was seen compared to vehicle control. No significant difference in pannus was detected between any treatment groups. Significant differences were observed between MMF and laquinimod treatment at 5 mg/kg indicating that the higher dose of the test article and MMF treatment were similar. There was a significant reduction in salivary gland inflammation as the higher dose of laquinimod resulted in a significantly lower score than did the lower dose. Joint inflammation was significantly reduced with laquinimod treatment at 5 mg/kg compared to vehicle. There was a trend towards reduction of joint pannus, however there were no other significant differences in the joint parameters between treatment groups. This lack of significant may be due to the high degree of variability in the data. Spleens were weighted and then splenocytes were isolated and counted. The splenocytes were then expressed as a percent of the total spleen cells. The spleen weights showed a trend towards reductions with all test article treatments, however this reduction did not achieve statistical significance. Therefore significant reductions in splenocyte counts with all treatments compared to vehicle. When the splenocytes were expressed as a percent of total spleen cells a significant reduction in percent splenocytes was detected with laquinimod treatment at 5 mg/kg compared to vehicle.

Example 2

Clinical Trial (Phase IIa)—Assessment of Laquinimod in Combination with Standard of Care for Treatment of Lupus Nephritis A multicenter, randomized, double-blind, placebo-controlled clinical trial is conducted to evaluate the safety, tolerability and clinical effect of laquinimod in active lupus nephritis patients, in combination with standard of care (Mycophenolate Mofetil and Steroids).

Study Population and Number of Subjects

Approximately 45 Systemic Lupus Erythematosus patients with active lupus nephritis (LN) are enrolled. [ISN/RPS 2003 classification of lupus nephritis—classes III (A or A/C), IV-S or IV-G (A or A/C), or class V—pure or in combination with class III or IV].

Study Duration

The overall study duration is up to 32 weeks, with the screening phase being up to 4 weeks, the treatment period being 24 weeks and the follow-up period being 4 weeks for all subjects who complete the 24-week treatment period or subjects who prematurely discontinue treatment prior to Week 24 visit.

Investigational Medicinal Product and Dosage

Laquinimod/Matching Placebo

Capsules containing laquinimod 0.5 mg and/or matching placebo are administered orally once daily:
1. Laquinimod 0.5 mg arm—1 capsule of laquinimod 0.5 mg and 1 matching placebo capsule.
2. Laquinimod 1 mg arm—2 capsules of laquinimod 0.5 mg.
3. Placebo arm—2 capsules of placebo.

Mycophenolate Mofetil (MMF)

MMF tablets 500 mg. All treatment arms receive MMF at baseline and throughout the study to a target dose of 2 g/day.

Inclusion/Exclusion Criteria

Inclusion Criteria

All subjects must meet all the inclusion criteria below to be eligible:
1. Subject is diagnosed with SLE, who fulfilled at least 4 classification criteria (1997 revised) of the American College of Rheumatology for SLE by the time of screening visit. All subjects should have abnormal titers (at least 1 in 80) of anti-nuclear antibodies (at screening or documented anytime in the past) or anti-dsDNA antibodies at screening. [On a case by case basis it is possible to re-assess anti-nuclear antibodies or anti-dsDNA between screening and baseline].
2. Kidney biopsy within 6 months prior to baseline with a histological diagnosis of LN: (ISN/RPS 2003 classification of lupus nephritis) classes III (A or A/C), IV-S or IV-G (A or A/C), or class V—pure or in combination with class III or IV. Kidney biopsy should be documented with a pathology report.
3. Clinically active LN as evident by protein to creatinine ratio ≥1, for LN class III, IV or [class V in combination with class III or IV] or protein to creatinine ratio ≥2 for LN class V, at screening or anytime between screening and baseline.

Eligibility is determined based on protein to creatinine ratio of spot urine collection and protein to creatinine ratio of 24 hours urine collection. Both assessments should comply with the above criteria.
4. Subjects must be between the ages of 18 and 75 years inclusive.
5. Subjects are willing and able to provide a written, informed consent.

Exclusion Criteria

Any of the following excludes the subject from entering the study:
1. GFR ≤30 ml/min/1.73 m$^2$ as calculated by MDRD formula at screening visit.
2. Dialysis within the last month prior to screening or scheduled to receive dialysis.
3. Previous kidney transplant or planned transplant.
4. Subjects with hemoglobin <8.5 g/dl or neutrophils <1300/mm$^3$ or platelets <50,000/mm$^3$, at screening.
5. Any previous diagnosis of drug induced lupus.
6. Subjects with severe, unstable and/or progressive CNS lupus and/or associated with significant cognitive impairment, upon Investigator's judgment.
7. Subjects with a clinically significant or unstable medical or surgical condition that, in the Investigator's opinion, would preclude safe and complete study participation, as determined by medical history, physical examinations, electrocardiogram (ECG), laboratory tests or imaging. Such conditions may include:
   a. A cardiovascular or pulmonary disorder that cannot be well-controlled by standard treatment permitted by the study protocol.
   b. Metabolic or hematological diseases.
   c. Any form of acute or chronic liver disease including hepatitis B antigen (HBsAg) or anti-hepatitis C virus (anti-HCV) seropositive subjects.
   d. Known Human immunodeficiency virus (HIV) positive status.
   e. Subjects with known active tuberculosis.
   f. Systemic infection at screening.
   g. A history of drug and/or alcohol abuse.
   h. A current major psychiatric disorder.
8. MMF/steroids specific exclusion criteria:
   a. Pancreatitis within 6 months prior to screening.
   b. Gastrointestinal hemorrhage within 6 months prior to screening.
   c. Peptic ulcers (unhealed) within 3 months prior to screening.
   d. Subject weight >120 kg (265 lb).
9. Subjects with a ≥2.5× upper limit of normal (ULN) serum elevation of either ALT or AST at screening.
10. Subjects with a ≥2× upper limit of normal direct or total bilirubin at screening.
11. Subjects diagnosed with Diabetes Mellitus, or Anti-Neutrophil Cytoplasmic Antibodies (ANCA) Vasculitis.
12. Medical condition, other than SLE that requires chronic treatment with immunosuppressive drugs or systemic corticosteroids (not including inhaled steroids).
13. Subjects with a history of malignancy within 5 years from screening with the exception of basal cell carcinoma (completely excised).
14. Women who are pregnant or nursing at the time of screening, or who intend to be during the study period.
15. Women of child-bearing potential (female subjects not of childbearing potential defined as post-menopausal for at least 12 months), who do not practice an acceptable method of birth control [acceptable methods of birth control in this study are: surgical sterilization, intrauterine devices, oral contraceptive, contraceptive patch, long-acting injectable contraceptive, partner's vasectomy, a double-protection method (condom or diaphragm with spermicide)]. Hormonal contraception must be accompanied by an additional barrier method of birth control (condom).

16. Subjects treated with MMF dose ≥2 g/day anytime between 31 days and 90 days prior to baseline or MMF dose >2 g/day within 30 days prior to baseline.
17. Subjects treated with oral corticosteroids at doses higher than 20 mg/day of prednisolone/prednisone (or equivalent) anytime between 8 and 90 days prior to baseline or prednisolone/prednisone dose (or equivalent) >40 mg/day within 7 days prior to baseline or any IV or IM steroid dose within 90 days prior to baseline.
18. Subjects treated with Azathioprine, MTX, Cyclosporine or Tacrolimus within 2 weeks prior to baseline.
19. Subjects treated with cyclophosphamide within 12 weeks prior to screening.
20. Subjects treated with Rituximab, abatacept, intravenous immune globulin (IV Ig), plasmapheresis or any other biologic therapy within 24 weeks prior to screening.
21. Subjects treated with alkylating agents (other than cyclophosphamide such as: nitrogen mustard, chlorambucil, vincristine, procarbazine or etopside) within 52 weeks prior to screening.
22. Subjects who received any investigational medication within 24 weeks prior to screening.
23. Use of inhibitors of CYP3A4 within 2 weeks prior to baseline visit (1 month for fluoxetine).
24. Use of amiodarone within 2 years prior to screening visit.
25. A known drug hypersensitivity that would preclude administration of study medications, such as known hypersensitivity to MMF, corticosteroids or hypersensitivity to: mannitol, meglumine or sodium stearyl fumarate.
26. Subjects unable to comply with the planned schedule of study visits and study procedures.

Study Design

This is a Phase IIa, randomized, double-blind, placebo-controlled study to assess the safety, tolerability and clinical effect of laquinimod in active lupus nephritis patients in combination with standard of care (MMF and steroids). This study evaluates the biomarkers, clinical effect, the safety and tolerability of two doses of laquinimod (0.5 mg and 1 mg/day) in subjects with active lupus nephritis in combination with standard of care (MMF and steroids).

All randomized subjects receive MMF at baseline. In addition, Methylprednisolone IV is administered at the site for all randomized subjects. Also, Prednisone/prednisolone is provided to all randomized subjects under prescription.

In addition to MMF, methylprednisolone and prednisone/prednisolone, all randomized subjects receive at baseline either laquinimod 0.5 mg, laquinimod 1 mg or matching placebo. Laquinimod/placebo capsules should be taken orally at the same time every day.

Laquinimod/placebo and MMF may be taken simultaneously or with time gap, (note that laquinimod/placebo is taken once daily, whereas MMF should be taken twice daily).

Subjects are assessed for study eligibility up to 4 weeks prior to baseline. Eligible subjects are initially randomized in a 1:1 ratio into one of the following two treatment arms:

1. Laquinimod 0.5 mg and mycophenolate mofetil (target dose—2 g/day) and IV methylprednisolone 500 mg/day for 3 days followed by oral prednisolone/prednisone (initial dose—40 mg/day).
2. Placebo for laquinimod and mycophenolate mofetil (target dose 2 g/day) and IV methylprednisolone 500 mg/day for 3 days followed by oral prednisolone/prednisone (initial dose—40 mg/day).

Enrollment to the 1 mg laquinimod dose group is initiated following the approval of the study Safety Committee, based on data of at least 10 subjects who have completed at least 4 weeks of treatment.

Upon approval, randomization into one of the following three treatment arms occurs in a ratio that allows for reaching an overall target enrollment of approximately 15 subjects per treatment arm. Drop-outs are not replaced.

1. Laquinimod 0.5 mg and mycophenolate mofetil (target dose—2 g/day) and IV methylprednisolone 500 mg/day for 3 days followed by oral prednisolone/prednisone (initial dose—40 mg/day).
2. Laquinimod 1 mg and mycophenolate mofetil (target dose—2 g/day) and IV methylprednisolone 500 mg/day for 3 days followed by oral prednisolone/prednisone (initial dose—40 mg/day).
3. Placebo for laquinimod and mycophenolate mofetil (target dose—2 g/day) and IV methylprednisolone 500 mg/day for 3 days followed by oral prednisolone/prednisone (initial dose—40 mg/day).

All study investigators are informed of the initiation of screening and/or randomization for the 1 mg dose group. All subjects in the screening phase are randomized, if eligible, to any of the three treatment arms.

Scheduled in-clinic visits is conducted at screening, baseline and at Weeks 1, 2, 3, 4, 6, 8, 10, 12, 16, 20, 24 and a follow-up visit at Week 28.

At the baseline visit, in addition to laquinimod/placebo, all subjects receive MMF 500 mg, two times daily (BID), which is increased to 1 g BID on Week 1. In addition, all receive IV methylprednisolone 500 mg/day for 3 days followed by 40 mg/day oral prednisolone/prednisone, which is tapered to not more than 10 mg/day by the end of Week 20, on a fixed steroid tapering regimen).

TABLE 1

Treatment medications and dosage regimen throughout the study

| | MMF | IV steroids | PO steroids | Laquinimod/PLC |
|---|---|---|---|---|
| Days 1-3 | 500 mg BID first dose in clinic | 500 mg/day in clinic | None | 0.5 mg, 1 mg or PLC 2 capsules once daily first dose in clinic |
| Day 4 to visit Week 1 | 500 mg BID | None | 40 mg/day in | 0.5 mg, 1 mg or PLC 2 capsules once daily |
| Visit Week 1 to visit Week 24 | 1 g BID | None | According to fixed tapering scheme | 0.5 mg, 1 mg or PLC 2 capsules once daily |
| Visit Week 24 to visit Week 28 | 1 g BID | None | Stable | None |

Treatment with laquinimod/placebo is discontinued on visit Week 24, and a follow-up/study completion visit is conducted at Week 28. Subjects, who early terminated the study prior to visit Week 24, preferably show up for a follow-up visit within 4 weeks of the early termination visit.

Unscheduled visits for safety or for any other reason may be conducted at any time during the study.

During the study period the British Isles Lupus Assessment Group (BILAG) 2004 score and the Patient and Evaluator Global Assessment Scores (PGA, EGA) are assessed as well as routine safety laboratory tests, PK analysis [laquinimod, and MMF], disease-related immunology tests and biomarkers.

Combination with Standard of Care

Lupus nephritis is one of the most severe manifestations of SLE and requires immediate treatment to restore renal function, prevent further deterioration and improve prognosis, hence all subjects enrolled to this trial receive the standard of care treatment [MMF and steroids] in addition to laquinimod/placebo.

MMF, although not specifically indicated for the treatment of lupus nephritis, is considered a standard of care for the above target population, for its perceived clinical efficacy and relatively favorable safety profile (Ginzler, 2005; Chan, 2000; Appel, 2007; Isenberg, 2008).

Standard MMF dosing for induction of response in lupus nephritis ranges between 2-3 g/day. All subjects enrolled in this trial receive a target dose of 2 g/day. In case of lack of response, as defined by the protocol, Investigators may increase the dose to 3 g/day.

MMF is widely used in combination with oral corticosteroids (0.5-1 mg/kg), while the corticosteroids are gradually being tapered down (Boumpas, 2005). As steroids may have confounding effect on the analysis of the trial and in order to minimize variability in steroid dosing and tapering all subjects enrolled to this trial receive IV steroids (500 mg/day) for the first three days of the trial followed by a fixed oral dose of prednisone/prednisolone 40 mg/day. Oral steroids are tapered according to a predetermined gradual tapering down scheme to not more than 10 mg/day by the end of Week 20.

The tapering down scheme is in an accepted standard tapering regimen and is used to standardize treatment in the study, hence reducing variability. Investigators, upon their clinical judgment, may choose to deviate from this fixed scheme, based on the individual subject response to treatment. Such subjects are allowed to continue their participation in the trial, yet are defined as protocol violators and/or treatment failures.

Dose Selection and Sequential Cohort Enrollment

Pre-clinical and clinical data suggest that the effect of laquinimod is dose dependent, hence supporting the evaluation of escalating doses.

The highest doses of laquinimod assessed to date, 1.2 mg and 2.4 mg, were studied in healthy volunteers and MS subjects (studies 99506202 and TQT-LAQ-122). Doses up to 2.4 mg/day were tolerated in healthy volunteers, while 2.4 mg/day resulted in elevation of markers of inflammation in MS patients, without clinical signs and symptoms.

For this study, laquinimod doses of 0.5 mg/day and 1 mg/day were chosen, which are believed to provide a reasonable therapeutic range.

As this is the first study to assess the safety, tolerability and clinical effect of laquinimod in active lupus nephritis patients and since limited data exists to date with higher doses of laquinimod, a sequential enrollment approach is applied. Subjects are initially randomized in a 1:1 ratio into one of two treatment arms—standard of care with laquinimod 0.5 mg and standard of care with placebo. Enrollment to the 1 mg dose group is initiated only following the approval of a Safety Committee, based on data of at least 10 subjects who have completed at least 4 weeks of treatment.

PK Analysis

Blood samples for PK evaluation are collected from all subjects as follows:
1. Visit Week 4—full PK profile (laquinimod and MMF) at the following times: pre-dose, 15, 30 min and 1, 1.5, 2, 3, 4, 6, 8, 12 and 24 hours post dosing.
2. Visit Weeks 12 and 24—prior to dosing (trough plasma levels—laquinimod and MMF).
3. Visit Week 28 (MMF)— prior to dosing (trough plasma levels—MMF).

Pharmacogenetic Sub Study

Blood samples for the pharmacogenetic sub-study are collected from all subjects who signed the separate informed consent form and upon ethics committee approval.

Previous and Concomitant Medication/Therapies

Any medication/treatment for SLE, unless otherwise specified as an exclusion criterion, is allowed preceding entry into the study (e.g. —antimalarials, NSAIDs, COX2 inhibitors, statins, ACE inhibitors, ARBs, corticosteroids, oral anticoagulants and bisphosphonates).

Mycophenolate Mofetil (MMF) Allowed During the Study
1. Dosing of MMF starts at 500 mg BID for the first week increasing to 1 g BID in the second week and throughout the study.
   a. For subjects already treated with MMF prior to baseline, as allowed by the clinical protocol:
      i. MMF dose=2 g—continue MMF 2 g for the remaining of the study.
      ii. MMF dose >1 g and <2 g—increase MMF to 2 g at baseline and continue for the remaining of the study.
      iii. MMF dose ≤1 g—continue according to protocol.
2. MMF dose can be reduced to a minimum of 1 g/day, at the investigators' discretion, in cases of intolerance to MMF.
3. Subjects with lack of response as defined by the protocol following 12 weeks of treatment are allowed to increase the MMF dose to 1.5 mg BID. These subjects are regarded as treatment failures but may continue their participation in the trial. Lack of response is defined as: protein to creatinine ratio >3 from Week 12 onwards and did not decrease by ≥20% compared to baseline (confirmed by repeated measurement within 2 weeks. At least 1 of the measurements should be a 24 hour urine collection).
4. MMF dose >2 g/day anytime during the first 24 weeks of treatment is regarded as a treatment failure.
5. In case of absolute neutrophil count <1300/mm3, dosing with MMF should either be interrupted or reduced.
6. In case of absolute neutrophil count <1000/mm$^3$, study medications (laquinimod/placebo and MMF) should be stopped and the subject should prematurely terminate his/her participation in the study.
7. An MMF dose reduction to <1 g/day, for any reason, for more than a total of 14 days during the treatment phase or a temporary dose interruption for more than a total of 7 days, are regarded as major protocol violations. Subjects exceeding the above parameters may continue their participation in the trial based on the Investigator's clinical judgment.
8. Dosing regimen may be changed (without changing the total daily dose) from BID to three times daily (TID), in order to reduce side effects, (at the Investigator's discretion).
9. MMF is also administered during the follow up period.

Corticosteroids Allowed During the Study
1. All subjects receive IV methylprednisolone (500 mg/day for 3 days) upon randomization followed by a dose of 40 mg/day of oral prednisolone/prednisone. This dose is tapered down according to a pre-defined tapering down scheme shown in Table 2. [On Baseline visit IV methylprednisolone should be administered following post dose vital signs].

TABLE 2

Steroid Tapering Scheme

| Weeks | Prednisolone dose (mg) | Disease exacerbation/lack of response |
|---|---|---|
| | | No    Yes |
| Days 1-3 | | IV methylprednisolone 500 mg |
| Days 4-7 | 40 | Go to next  It is allowed only |
| 2 | 40 | step  once to maintain |
| 3 | 35 | the previous week |
| 4 | 35 | dose for |
| 5 | 30 | additional two |
| 6 | 30 | weeks and continue |
| 7 | 25 | taper by not more |
| 8 | 25 | than 5 mg every 2 |
| 9 | 20 | weeks |
| 10 | 20 | Dose higher by more |
| 11 | 17.5 | than 5 mg compared |
| 12 | 17.5 | with the week dose |
| 13 | 15 | or >40 mg or any IV |
| 14 | 15 | or IM dose will |
| 15 | 12.5 | result in treatment |
| 16 | 12.5 | failure |
| 17 | 10 | |
| 18 | 10 | |
| 19 | ≤10 | |
| 20 | ≤10 | |
| 21-28 | Stable | |

2. Subjects unable to comply with the pre-defined tapering down scheme—receive higher doses than allowed by the protocol or unable to reach prednisolone/prednisone dose ≤10 mg day at the end of Week 20 are allowed to continue their participation in the trial but are regarded as major protocol violators and treatment failures.
3. Subjects who taper down their steroid dose by increments larger than 5 mg/day compared to the previous dose or who do not maintain the same dose for at least 2 weeks are allowed to continue their participation in the trial but are regarded as major protocol violators. [tapering from 20 mg prednisolone/prednisone to 15 mg prednisolone/prednisone, not via 17.5 mg or from 15 mg to 10 mg not via 12.5 mg is allowed, hence enabling reaching 10 mg prednisolone/prednisone as early as Week 13].
4. The dose of corticosteroids can be decreased to the lowest possible dose (to a dose lower than 10 mg/day), at the Investigator's discretion and as long as within the protocol limitations for tapering down.
5. Use of IV or IM steroids (other than allowed by the protocol) during the study treatment period is regarded as major protocol violation and a treatment failure, yet subjects may continue their participation in the trial. Intraarticular or inhaled steroids can be used during the treatment period per the Investigator's discretion and is not regarded as a protocol violation.
6. From visit Week 20 to visit Week 24, subjects should be maintained on a stable steroid dose. [Defined as <5 mg prednisone/prednisolone change from Week 20 dose]. Dose increase not allowed by the protocol is regarded as treatment failure.

Other Medications

1. ACE inhibitors/ARBs should be kept stable throughout the study or otherwise result in a protocol violation. New treatment or dose increase throughout the treatment period is regarded as treatment failure.
2. New treatment or change in dose of antimalarials or statins is allowed, at the Investigator's discretion, at the first 4 weeks of the treatment period, but kept stable throughout the trial.
   New treatment or change in dose following the first 4 weeks is regarded as protocol violation.
3. Bone protection therapy (e.g., bisphosphonates) is allowed throughout the trial.
4. The use of CYP1A2 substrates (e.g. Warfarin) during the treatment period is permitted, however subjects treated with these medications should be monitored for possible reduction in their effect.
5. No drugs for the treatment of lupus nephritis other than those specifically described above are allowed during the course of the study.
6. New or change in dose/dose regimen of non-steroidal anti-inflammatory drugs (NSAIDs) or Cox2 inhibitors should be avoided during the treatment period.
7. Rescue therapy for SLE (any new medication/treatment or dose increase, not allowed by the protocol, administered for renal or non-renal manifestations), throughout the study treatment period, results in major protocol violation and is regarded as a treatment failure. Any new biologic treatment or new immunosuppressive or cytotoxic drug, IV-Ig or plasmapheresis, throughout the study treatment period, is regarded as treatment failure and results in early termination.
8. Inhibitors of CYP3A4 are not allowed throughout the study (2 weeks prior to baseline until the end of the follow up period). In case of treatment discontinuation of laquinimod, CYP3A4 inhibitors should be avoided for up to 30 days.
9. The use of live attenuated vaccines should be avoided throughout the study (including following up period).

Follow Up Period

All attempts are made to maintain a stable dose of MMF, steroids or any other drug prescribed during the study treatment period, throughout the follow-up period.

Pre-Defined Withdrawal Criteria/Treatment Failure

Any of the following results in early termination from the study:
1. Increase in serum creatinine without improvement in proteinuria from 8 weeks onward (confirmed by repeated measurement within 2 weeks), defined as:
   a. Serum creatinine >1.3 mg/dL that is at least 25% higher than the baseline value; and
   b. Protein to creatinine ratio did not decrease by ≥25% compared to baseline (confirmed by 24 hours urine collection in at least one of the measurements)
1. Doubling of protein to creatinine ratio compared to baseline and protein to creatinine ratio >3 from Week 8 onwards (confirmed by repeated measurement within 2 weeks. At least one of the measurements should be a 24 hours urine collection).

Outcome Measures

Response Definitions

1. Complete response (CR)—protein to creatinine ratio <0.5 and [decreased serum creatinine by at least 25% compared to baseline or serum creatinine <1.3 mg/dL].
2. Partial response (PR)— criteria for complete response are not met and at least 50% decrease in protein to creatinine ratio and protein to creatinine ratio <3 with stable serum creatinine (serum creatinine <1.3 mg/dL or did not increase by more than 10% from baseline).
   Analyses is based on 24 hours urine collection at baseline, visit Week 12, visit Week 24/early termination (prior to visit Week 24), visit Week 28 or at any other scheduled or unscheduled visit for confirmation of pre-defined withdrawal criteria or lack of response.
3. BILAG renal response is defined as change from renal A or B at baseline to C or D.
4. BILAG Substantial Responder (SR) is defined as all systems at last observed value (LOV) are C or D/E providing at least one system is A or B at baseline.

Clinical Effect Outcome Measure
Renal—System
1. Proportion of Subjects with Complete or Partial Response at Week 24 and the Lack of Treatment Failure The number and percent of subjects, calculated from the randomized population, who are in complete or partial response, are presented both in tabular and graphical forms by treatment group.

Analyses are based on protein to creatinine ratio of spot urine collection from the appropriate visits. Analyses based on albumin to creatinine ratio (spot urine collection) and total protein to creatinine and albumin to creatinine 24 h urine collection is also performed.
2. Proportion of Subjects with Complete Response at Week 24 and the Lack of Treatment Failure The number and percent of subjects, calculated from the randomized population, who are in complete response, are presented both in tabular and graphical forms by treatment group.
3. Proportion of BILAG Renal Response at Week 24 and the Lack of Treatment Failure The number and percent of subjects, calculated from the randomized population, who are in BILAG renal response at Week 24 are presented both in tabular and graphical forms by treatment group.
4. Proportion of Subjects Treated with Prednisone/Prednisolone Dose ≤10 mg by the End of Week 20 Who Maintain a Stable Dose up to Week 24.

The number and percent of subjects, calculated from the randomized population who were treated with prednisone/prednisolone dose not more than 10 mg/day by the end of Week 20 and maintained this dose stable until Week 24 is presented both in tabular and graphical forms by week in trial and treatment group.
5. Time to Complete or Partial Response and the Lack of Treatment Failure Each subject is assigned with a time in which complete or partial response was achieved in the lack of treatment failure. Early termination or completer subject is right censored with their last available time in the trial. The Kaplan Meire estimates is presented using a survival curve.
6. Change in Protein to Creatinine Ratio/24 Hours Urine Protein at Week 24.

Descriptive statistics of protein to creatinine ratio/24 hours urine protein at Week 24 as well as change from baseline are presented by treatment group in tabular and graphical forms.
7. Change in Serum Creatinine and Glomerular Filtration Rate (GFR) (by applying the MDRD Formula) at Week 24

Descriptive statistics of serum creatinine and GFR (by applying the MDRD formula) at Week 24 as well as change from baseline are presented by week in trial and treatment group in tabular and graphical forms General SLE and Biomarkers
1. Proportion of Substantial BILAG Responders at Week 24:

The number and percent of subjects, calculated from the randomized population, who are with substantial BILAG response at Week 24 are presented in both tabular and graphical forms by treatment group.
2. Change in Anti-dsDNA, C3, C4, CH50 and Anti C1q at Week 24.

Descriptive statistics of anti-dsDNA, C3, C4, CH5 and anti-C1q at Week 24 as well as change from baseline are presented by group in tabular and graphical forms. Similarly, the number and percent of subjects shifted from normal at baseline to abnormal are presented by week in trial and treatment group in tabular forms.
3. Proportion of Subjects with New BILAG A or B Anytime During ht Study.

The number and percent of subjects, calculated from the randomized population, who experienced a new BILAG A or B in any system throughout the treatment period (24 weeks), are presented both in tabular and graphical forms by treatment group.
4. Change in Patient and Evaluator Global Assessment (PGA & EGA) at Week 24.

Descriptive statistics of PGA and EGA at Week 24 as well as change from baseline are presented by treatment group in tabular and graphical forms.
5. Cytokines and Chemokines (Serum and PBMC's Supernatant and Urine), Gene Expression and Cell Surface Markers (PBMC's).

Descriptive statistics of biomarkers as well as change from baseline are presented by week in trial and treatment group in tabular and graphical forms.

Safety and Tolerability Outcome Measures
1. Incidence, frequency and severity of adverse events (AEs).
2. Changes in clinical laboratory values.
3. Changes in vital signs.
4. Changes in ECG.
5. Proportion of subjects who prematurely discontinue treatment.
6. Proportion of subjects who prematurely discontinue treatment due to AEs.
7. Time to premature treatment discontinuation.
8. Time to premature treatment discontinuation due to AEs.

Tolerability analysis is based on the number (%) of subjects who failed to complete the study, the number (%) of subjects who failed to complete the study due to adverse events.

Results

This study assesses the efficacy, tolerability and safety of daily dose of 0.5 mg and 1.0 mg laquinimod as compared to placebo in active lupus nephritis patients, in combination with standard of care (Mycophenolate Mofetil and Steroids). The results indicate that the effect of the combination of laquinimod, MMF and steroids on active lupus nephritis is significantly more than the additive effect of each agent alone.

Daily oral administration of 0.5 mg or 1 mg laquinimod in combination with standard of care (Mycophenolate Mofetil and Steroids) is effective to treat active lupus nephritis. Further, the amounts of each agent when taken together are more effective to treat the active lupus nephritis in the subject than when each agent is administered alone.

Daily oral administration of 0.5 mg or 1 mg laquinimod in combination with standard of care (Mycophenolate Mofetil and Steroids) results in a complete response by the subject, wherein complete response (CR) is defined as: protein to creatinine ratio <0.5 and [decreased serum creatinine by at least 25% compared to baseline or serum creatinine <1.3 mg/dL].

Daily oral administration of 0.5 mg or 1 mg laquinimod in combination with standard of care (Mycophenolate Mofetil and Steroids) reduces proteinuria in the subject.

Daily oral administration of 0.5 mg or 1 mg laquinimod in combination with standard of care (Mycophenolate Mofetil and Steroids) results in a partial response by the subject, wherein partial response (PR) is defined as: criteria for complete response are not met and at least 50% decrease in protein to creatinine ratio and protein to creatinine ratio <3 with stable serum creatinine (serum creatinine <1.3 mg/dL or did not increase by more than 10% from baseline).

Daily oral administration of 0.5 mg or 1 mg laquinimod in combination with standard of care (Mycophenolate Mofetil and Steroids) reduces the subject's protein to creatinine ratio by at least 50% as compared to baseline during the study period.

Daily oral administration of 0.5 mg or 1 mg laquinimod in combination with standard of care (Mycophenolate Mofetil and Steroids) reduces the subject's protein to creatinine ratio to no more than 0.3 during the study period.

Daily oral administration of 0.5 mg or 1 mg laquinimod in combination with standard of care (Mycophenolate Mofetil and Steroids) increases the subject's glomerular filtration rate (GFR) by at least 25% as compared to baseline during the study period. Daily oral administration of 0.5 mg or 1 mg laquinimod in combination with standard of care (Mycophenolate Mofetil and Steroids) increases the subject's glomerular filtration rate (GFR) to greater than 70 ml/min/1.73 m$^2$ during the study period.

Daily oral administration of 0.5 mg or 1 mg laquinimod in combination with standard of care (Mycophenolate Mofetil and Steroids) limits the decrease of the subject's glomerular filtration rate (GFR) to no more than 10% as compared to baseline during the study period.

Daily oral administration of 0.5 mg or 1 mg laquinimod in combination with standard of care (Mycophenolate Mofetil and Steroids) eliminates urinary sediments.

Daily oral administration of 0.5 mg or 1 mg laquinimod in combination with standard of care (Mycophenolate Mofetil and Steroids) improves the subject's BILAG index during the study period.

Daily oral administration of 0.5 mg or 1 mg laquinimod in combination with standard of care (Mycophenolate Mofetil and Steroids) is well tolerated and has no toxicity.

Thus, these results show that administration of laquinimod in combination with standard of care (Mycophenolate Mofetil and Steroids) is effective to treat active lupus nephritis. Further, these results show that administration of laquinimod in combination with standard of care (Mycophenolate Mofetil and Steroids) is substantially more efficacious in treating of lupus nephritis than each agent when administered alone.

REFERENCES

1. "CELLCEPT®" in Physician's Desk Reference, Medical Economics Co., Inc., Montvale, N.J., 2009, 2622-2629.
2. "Lupus Nephritis" MedlinePlus Online, a service of U.S. National Library of Medicine, 8600 Rockville Pike, Bethesda, Md. 20894 and National Institutes of Health, Department of Health & Human Services, Accessed Feb. 19, 2010. (http://www.nlm.nih.gov/medlineplus/ency/article/000481.htm)
3. "Systemic Lupus Erythematosus" The Merck Manual, 17th ed. Mark H. Beers, MD, Robert Berkow, MD, eds. Whitehouse Station, N.J.: Merck Research Labs, 1999.
4. 0130282 99506202. A double blind, randomized, repeat-dose, dose escalation study of ABR-215062 versus placebo in healthy volunteers and patients with multiple sclerosis. Active Biotech Research AB, Sweden. Final Clinical Trial Report, January 2002.
5. 03506207. An open safety study on laquinimod (ABR-215062) in patients with multiple sclerosis. Active Biotech Research AB, Sweden. Final Clinical Trial Report, April 2007.
6. 0430067 275-1061-01. Determination of the effects of ABR-212616, ABR-215050, ABR-215062 and ABR-215757 on the activities of CYP1A2 and CYP3A4 in cryopreserved human hepatocytes. In Vitro Technologies, USA. Final Report, February 2004.
7. 0430518 275-1081-02. Determination of the effects of ABR-215062 on CYP1A2 and CYP3A4 in cryopreserved human hepatocytes. In Vitro Technologies, USA. Final Report, August 2004.
8. 9830089. PNU-215045, PNU-215062: Effects on cytochrome P450 enzymes in female Sprague Dawley rats. Lund Research Center AB, Active Biotech Group, Sweden. Final Report, November 1998.
9. 9830133. PNU-215062: Effects on cytochrome P450 enzymes in female Sprague Dawley rats. Lund Research Center AB, Active Biotech Group, Sweden. Final Report, November 1998.
10. A two-period, open-label, one-sequence crossover study in healthy subjects to assess the potential interaction of fluconazole on laquinimod pharmacokinetics. PRACS Institute Cetero Research, ND, USA. Final Report, June 2009.
11. Appel G B Dooley M A Ginzler E M. Mycophenolate mofetil compared with intravenous cyclophosphamide as induction therapy for lupus nephritis: Aspreva Lupus Management Study (ALMS) results. 47A of JASN, Vol. 18 Oct. 2007.
12. Austin H A, Balow J E. Diffuse proliferative Lupus Nephritis: Identification of specific pathologic features affecting renal outcomes. Kidney International 1984; 25:689-695.
13. Bevra Hahn. Systemic Lupus Erythematosus. In: Brauwald E., Fauci A S, Kasper D L, Hauser S L, Longo D L, Jameson J L, eds. Harrison's Principles of Internal Medicine. New York: McGraw-Hill Professional, 2001: 1922-28.
14. Boumpas D T. Optimum therapeutic approaches for Lupus Nephritis: What Therapy and for whom. Nature Clinical Practice Rheumatology. 2005; 1: 22-30.
15. Brent L H. Lupus Nephritis, Emedicine, 2008.
16. Chan T M Li F K Tang C S. Efficacy of mycofenolate mofetil in patients with diffuse proliferative Lupus Nephritis. N Eng J Med; 2000; 343: 1156-1162.
17. FDA 2005. Draft Guidance for Industry—Systemic Lupus Erythematosus—Developing Drugs for Treatment (http://www.fda.gov/downloads/Drugs/GuidanceComplianceRegulatoryInformation/Guidances/ucm072063.pdf).
18. Foster, Kirk MD; Markowitz, Glen S MD (2004) "A Revised Classification of Lupus Nephritis: In with the New" *Advances in Anatomic Pathology*: September 2004, Volume 11, Issue 5, pp 277-278.
19. Ginzler E M Dooley M A Aranow C. Mycophenolate Mofetil or intravenous Cyclophosphamide for Lupus Nephritis. N Eng J Med; 2005; 353: 2219-2228.
20. Isenberg D, Appeal G B, Contreras G, Dooley M A, Ginzler E M, Jayne D, Sanchez-Guerrero J, Wofsy D, Yu X, Solomons N. "Invludence of race/ethnicity on response to lupus nephritis treatment: the ALMS study. Rheumatology (Oxford). 2010 January; 49(1):128-40. Epug 2009 Nov. 20.
21. Kurucz I., S. Toth, K. Nemeth, K. Torok, V. Csillik-Perczel, A. Pataki, C. Salamon, Z. Nagy, J. I. Szekely, K. Horvath, and N. Bodor (2003) "Potency and specificity of the pharmacological action of a new, antiasthmatic, topically administered soft steroid, etiprednol dicloacetate (BNP-166)". *J Pharmacol Exp Ther.* 307(1):83-92.

22. Petri M. Epidemiology of systemic lupus erythematosus. Best Pract Res Clin Rheumatol 2002; 16(5):847-858.
23. Polman, C. et al., (2005) "Treatment with laquinimod reduces development of active MRI lesions in relapsing MS", Neurology. 64:987-991.
24. Sandberg-Wollheim M, et al. (2005) "48-week open safety study with high-dose oral laquinimod in patients", *Mult Scler.* 11:S154 (Abstract).
25. Sharabi A. A. Haviv, H. Zinger, M. Dayan and E. Moses (2006) "Amelioration of murine lupus by a peptide, based on the complementarity determining region 1 of an autoantibody as compared to dexamethasone: different effects on cytokines and apoptosis". *Clin. Immunology.* 119:146-155.
26. Sharabi A., H. Zinger, M. Zborowsky, Z. m. Sthoeger and E. Mozes (2006) "A peptide based on the complementarity-determining region 1 of an autoantibody ameliorates lupus by up-regulating CD4+CD25+ cells and TGB-B". *PNAS* 1103:8810-8815.
27. The American College of Rheumatology response criteria for proliferative and membranous renal disease in Systemic Lupus Erythemtosus. Arthritis Rheum; 54(2): 421-432.
28. TQT-LAQ-122. A Double-Blind, Randomized, Parallel Group, Thorough QT/QTc Trial in Healthy Men and Women to Assess the Effect of Laquinimod on Cardiac Repolarization Using a Clinical and a Supratherapeutic Dose Compared to Placebo, with Moxifloxacin as a Positive Control. PRACS Institute Cetero Research, ND, USA. Final Report, June 2009.
29. U.S. Pat. No. 6,077,851, issued Jun. 20, 2000 to Bjork, et al.
30. Weening J J et al on behalf of the International Society of Nephrology and Renal Pathology Society Working Group on the classification of lupus nephritis. The classification of glomerulonephritis in systemic lupus erythematosus revisited. Kidney International Journal 2004, 67; 521-530.
31. Yee C S, Caroline Gordon, et al. British Isles Lupus Assessment Group 2004 Index is valid for assessment of disease activity in SLE. Arthritis &Rheumatism. 2007; 56:4113-4119.
32. Yee C S, Caroline Gordon, et al. British Isles Lupus Assessment Group 2004 Index. A reliable tool for assessment of SLE activity. Arthritis &Rheumatism. 2006; 54:3300-3305.

What is claimed is:

1. A method of treating a subject afflicted with active lupus nephritis comprising administering to the subject daily between 0.5-1.0 mg of laquinimod or pharmaceutically acceptable salt thereof and between 1-3 g of mycophenolate mofetil, wherein the amount of laquinimod and the amount of mycophenolate mofetil when taken together are more effective to treat he subject than when each agent is administered alone.

2. The method of claim 1, wherein the pharmaceutically acceptable salt of laquinimod is laquinimod sodium.

3. The method of claim 1, wherein the daily administration laquinimod or pharmaceutically acceptable salt thereof is effected orally.

4. The method of claim 1, wherein the amount of laquinimod administered is 0.5 mg/day.

5. The method of claim 1, wherein the amount of laquinimod administered is 1.0 mg/day.

6. The method of claim 1, wherein the daily administration of mycophenolate mofetil is effected orally.

7. The method of claim 1, wherein the amount of mycophenolate mofetil administered is 2 g/day.

8. The method of claim 1, further comprising administering to the subject an amount of a steroid.

9. The method of claim 8, wherein the administration of the steroid is daily administration.

10. The method of claim 8, wherein the administration of the steroid is effected orally and/or intravenously.

11. The method of claim 8, wherein the amount of steroid administered is 500 mg/day methylprednisolone.

12. The method of claim 8, wherein the amount of steroid administered is 40 mg/day prednisolone and/or prednisone.

13. The method of claim 1, further comprising administration of angiotensin converting enzyme (ACE) inhibitors, angiotensin receptor blockers (ARBs), antimalarials, statins, cyclophosphamide, azathioprine, 6-mercaptopurine, abatacept, rituximab, belimumab, cyclosporine or other calcineurin inhibitors.

14. The method of claim 1, wherein the daily administration continues for at least 24 weeks.

15. The method of claim 1, wherein the subject is human.

* * * * *